United States Patent
Ellinger

[19]
[11] Patent Number: 6,047,041
[45] Date of Patent: Apr. 4, 2000

[54] APPARATUS AND METHOD FOR COMPARISON

[75] Inventor: Hunter Ellinger, Austin, Tex.

[73] Assignee: Scientific Measurement System, Austin, Tex.

[21] Appl. No.: 08/929,198

[22] Filed: Sep. 8, 1997

[51] Int. Cl.[7] .................................................. G01N 23/02
[52] U.S. Cl. .............................................. 378/58; 378/57
[58] Field of Search .................................. 378/57, 58, 59, 378/60, 61; 382/141, 149, 152; 364/468.15, 468.16, 468.17

[56] References Cited

U.S. PATENT DOCUMENTS

| | | | |
|---|---|---|---|
| 4,803,639 | 2/1989 | Steele et al. .............................. | 364/507 |
| 4,920,491 | 4/1990 | Eberhard et al. . | |
| 4,961,154 | 10/1990 | Pomerantz et al. ...................... | 364/522 |
| 4,969,110 | 11/1990 | Little et al. ............................... | 364/550 |
| 4,991,224 | 2/1991 | Takahashi .................................. | 382/26 |
| 5,023,895 | 6/1991 | McCroskey ................................ | 378/4 |
| 5,056,130 | 10/1991 | Engel ........................................ | 378/207 |
| 5,319,693 | 6/1994 | Eberhard et al. ........................ | 378/19 |
| 5,402,460 | 3/1995 | Johnson et al. .......................... | 378/10 |
| 5,475,726 | 12/1995 | Azevedo et al. ........................... | 378/4 |
| 5,506,785 | 4/1996 | Blank et al. ............................... | 364/468 |
| 5,515,160 | 5/1996 | Schulz et al. ............................. | 356/241 |
| 5,539,800 | 7/1996 | Katsevich et al. ....................... | 378/210 |
| 5,561,696 | 10/1996 | Adams et al. ............................. | 378/58 |
| 5,594,652 | 1/1997 | Penn et al. ........................ | 364/468.26 |
| 5,848,115 | 12/1998 | Little et al. ................................. | 378/4 |

*Primary Examiner*—David V. Bruce
*Attorney, Agent, or Firm*—J. Nevin Shaffer, Jr.; Shaffer & Culbertson, LLP

[57] ABSTRACT

A method of comparison includes the step (14) of obtaining an interior and exterior image of an object to be compared. A standard of measurements for an acceptable object is created in step (12). An automatic comparison is made in step (14) of the image of the object to be compared with the standard and a comparison report is generated in step (16) listing deviations of the image of the object to be compared from the standard for the acceptable object. An x-ray CT scanner (76) may be utilized for obtaining the images and the standard may be derived from an actual, acceptable object or from design specifications for acceptable objects. In a preferred embodiment, CAD designs are utilized to create the standards for comparison.

10 Claims, 5 Drawing Sheets

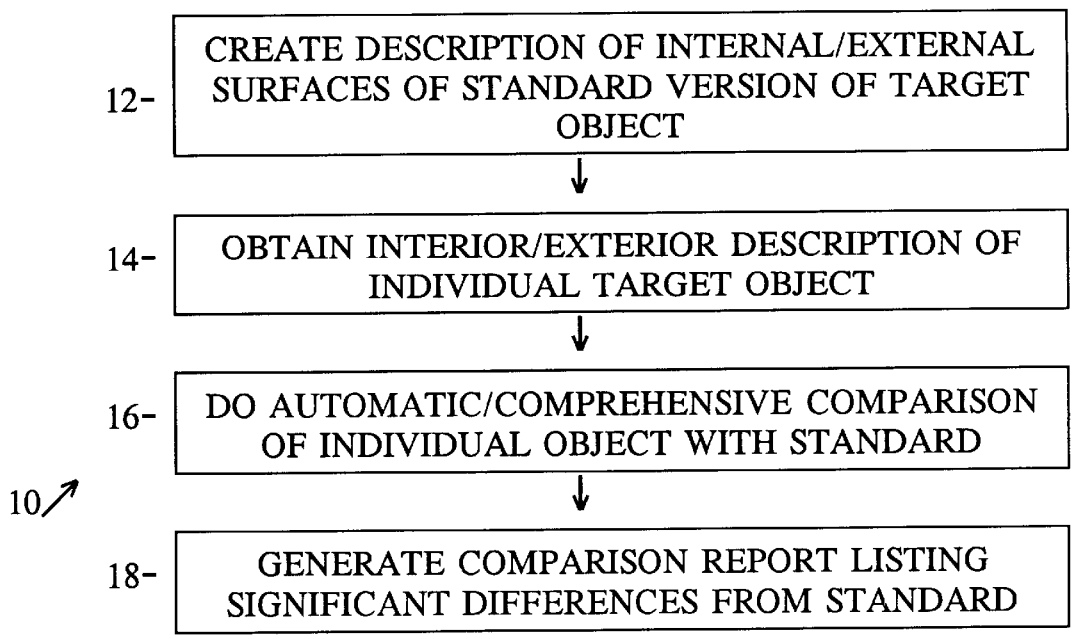
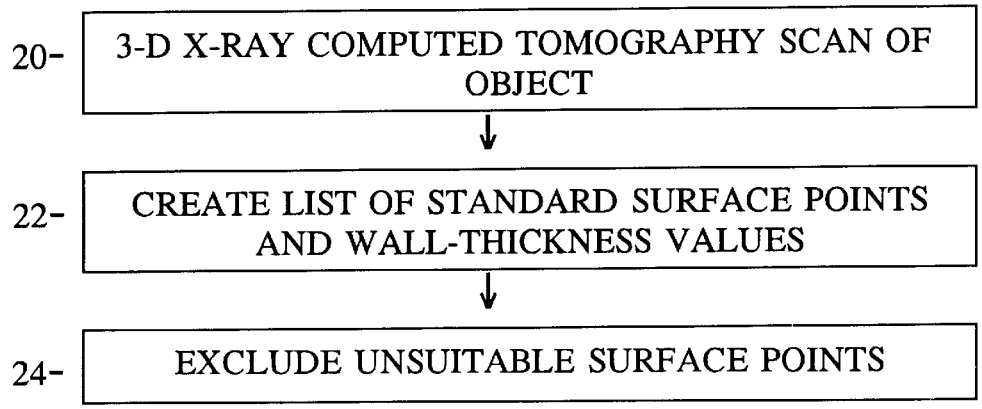

APPARATUS AND METHOD FOR COMPARISON

BACKGROUND OF THE INVENTION

This invention relates to an improved apparatus and method for comparison. In particular, this invention relates to an apparatus and method for comparing objects with a standard for the objects. More particularly, the invention relates to an improved apparatus and method for comparing actual parts with previously manufactured, acceptable parts and/or design specifications for acceptable parts.

It is often necessary and sometimes critical to determine how close a manufactured part comes to parts that have previously been determined to be acceptable or to the design of an acceptable part. It is not often possible to measure parts completely once manufactured so as to determine such important measurements as shape and wall thickness, heretofore, without destroying the part to be measured. Prior art devices have utilized computerized tomography to create scans of slices of a part. These prior art scans, however, result only in individual slices of a part which then are analyzed by an engineer. Because of the time consuming nature of the prior art scanning devices and the necessity for an engineer to review the scans, scans of only a limited number of predetermined "critical" specific locations have been analyzed in the past.

Thus, there is a need in the art for an apparatus and method wherein the whole part may be analyzed to determine the shape and wall thickness of the device throughout and compared to design specifications throughout. It, therefore, is an object of this invention to provide an improved apparatus and method for non-destructively comparing objects, such as manufactured parts, completely and automatically without need for engineering review of only a limited number of specific scans.

SHORT STATEMENT OF THE INVENTION

Accordingly, the method for comparison of the present invention includes the step of obtaining an interior and exterior image of an object to be compared. A standard of measurements for an acceptable object is then created and a comparison is automatically made between the image of the object to be compared and the standard. A resultant comparison report is generated listing the deviations of the image of the object from the standard for an acceptable object. In one embodiment, the step of obtaining an image comprises the step of conducting an x-ray CT scan of the entire object. Further, the step of creating a standard of measurements for an acceptable object includes the steps of creating a list of sample points at a specified maximum spacing for all surfaces of an acceptable object and creating a list of wall thickness at each sample point for an acceptable object. Further, the invention includes the steps of determining sample points which are not suitable for measurement of wall thicknesses and automatically excluding those points from comparison. Not suitable sample points are selected from a group including points in regions of rapid curvature, thickness for points where entry and exit normals differ significantly, points where thickness is too large to be relevant as a wall measurement and points near free edges. A step of creating a standard includes the steps of scanning a sample acceptable object of utilizing the design of an acceptable object to generate a sample point list. The sample point list is then transformed into sample scan coordinates for use in comparison with the image of the object to be compared. As will be discussed more fully hereafter, a variety of reports are then capable of being generated automatically.

In preferred embodiment, the object to be compared is a manufactured part and the image created is a 3-D image of the interior and exterior of the actual manufactured part.

An apparatus for comparing an actual part with an acceptable part includes an imaging device for obtaining an interior and exterior image of the actual part. A computer processor is utilized for storing a standard of measurements of the acceptable part, for translating the image into comparable measurements and for automatically comparing the measurements of the image with the standard. In one embodiment, the imaging means is an x-ray CT scanner. Additionally, in the apparatus, the standard of measurements of the acceptable part is derived from measurements of previously manufactured acceptable parts or from a CAD design. Additionally, the apparatus, in the preferred embodiment, includes a computer processor which makes at least 250,000 comparisons per minute.

BRIEF DESCRIPTION OF THE DRAWINGS

Other objects, features and advantages of the present invention will become more fully apparent from the following detailed description of the preferred embodiment, and the accompanying drawings in which:

FIG. 1 is a flow chart illustrating the steps for implementing the method of comparison of the present invention;

FIG. 2 is a flow chart illustrating the pre-scanning steps of the present invention;

DETAILED DESCRIPTION OF THE PREFERRED EMBODIMENT

The preferred embodiment of the present invention is illustrated by way of example in FIGS. 1–5. With specific reference to FIG. 1, a method for comparison of the present invention 10 includes the step 12 of creating a standard of measurements for an acceptable object. Next, step 14 includes obtaining an interior and exterior image of an object to be compared. Next, at step 16 an automatic comparison is made of the image of the object with the standard. Finally, at step 18, a comparison report is generated which lists the deviations of the image of the object from the standard for an acceptable object.

Referring now to FIG. 2, the step 14 of obtaining an image of the interior and exterior of an object may be accomplished by any means known in the art. A preferred embodiment of step 14 is to utilized in, step 20, an x-ray CT scanner so as to obtain a 3D scan of the entire object to be compared. Further, the step 12 of creating the standard of measurements for an acceptable object includes the step 22 of creating a list of sample points at a specified maximum spacing for all surfaces of an acceptable object and a list of wall thicknesses at each sample point for an acceptable object. It is also additionally preferable to include the step 24 of determining sample points which are not suitable for measurement of wall thickness and providing for automatically excluding those points from comparison. While any desired criteria can be developed for determining which sample points are not suitable, in a preferred embodiment, not suitable sample points are selected from a group including points in regions of rapid curvature, thickness for points where entry and exit normals differ significantly, points where thickness is too large to be relevant as a wall measurement and points near free edges.

Figure 3:
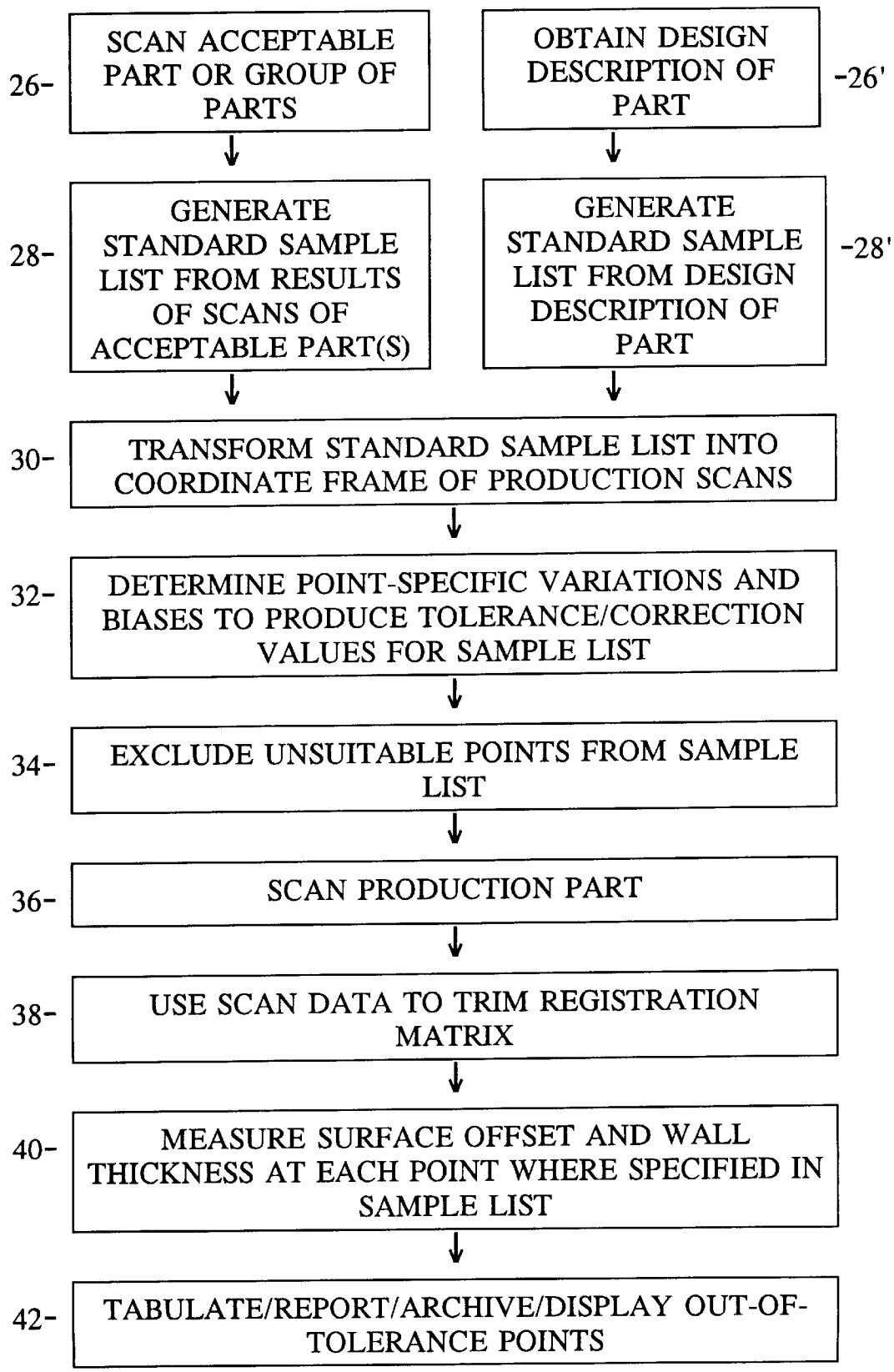
FIG. 3 is a flow chart illustrating the initializing steps of the present invention.
Figure 4:
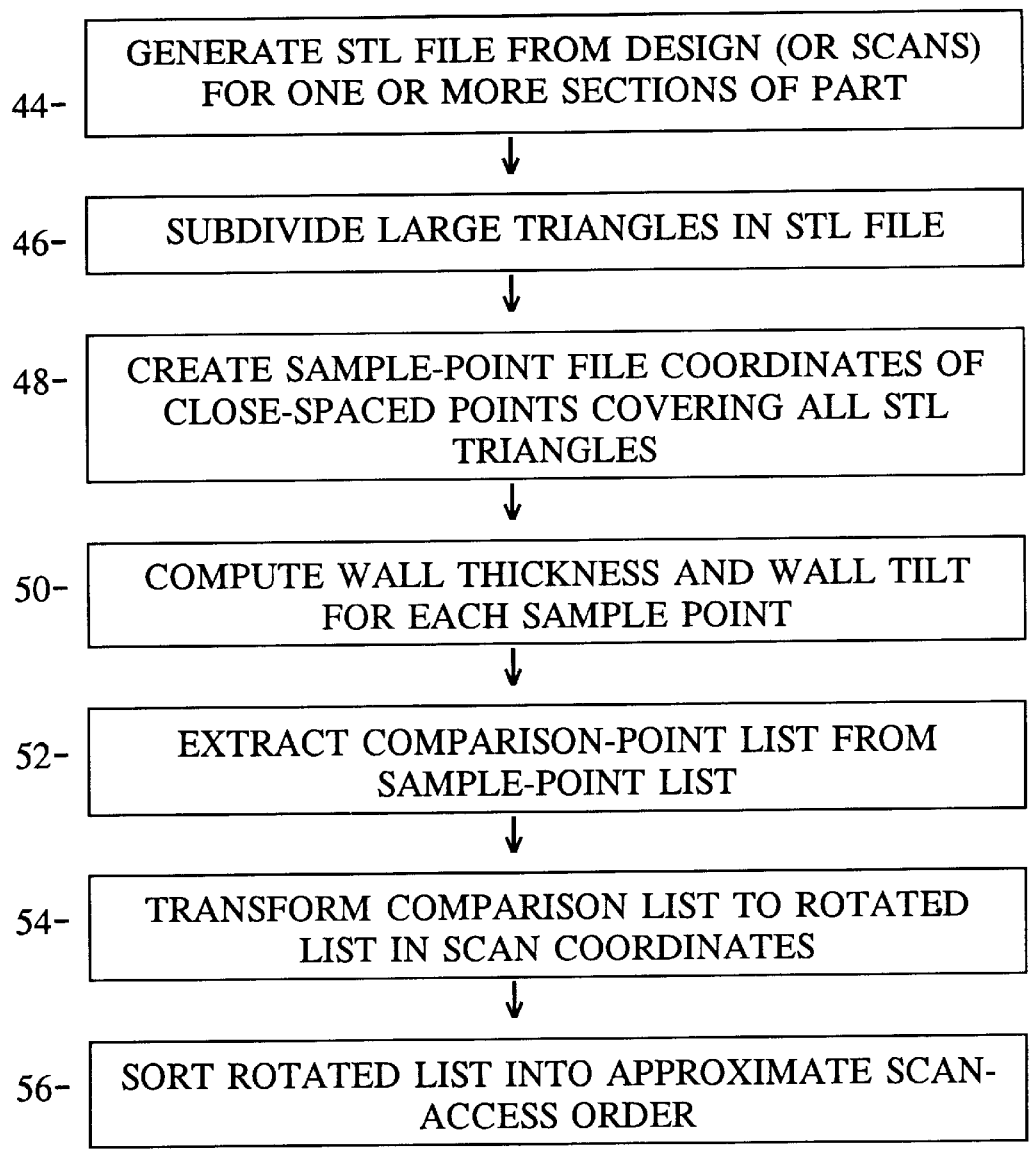
FIG. 4A is a flow chart illustrating the method of the present invention when a CAD model is available.
FIG. 4B is a flow chart illustrating the method of the present invention when a production part is scanned.
Figure 4:
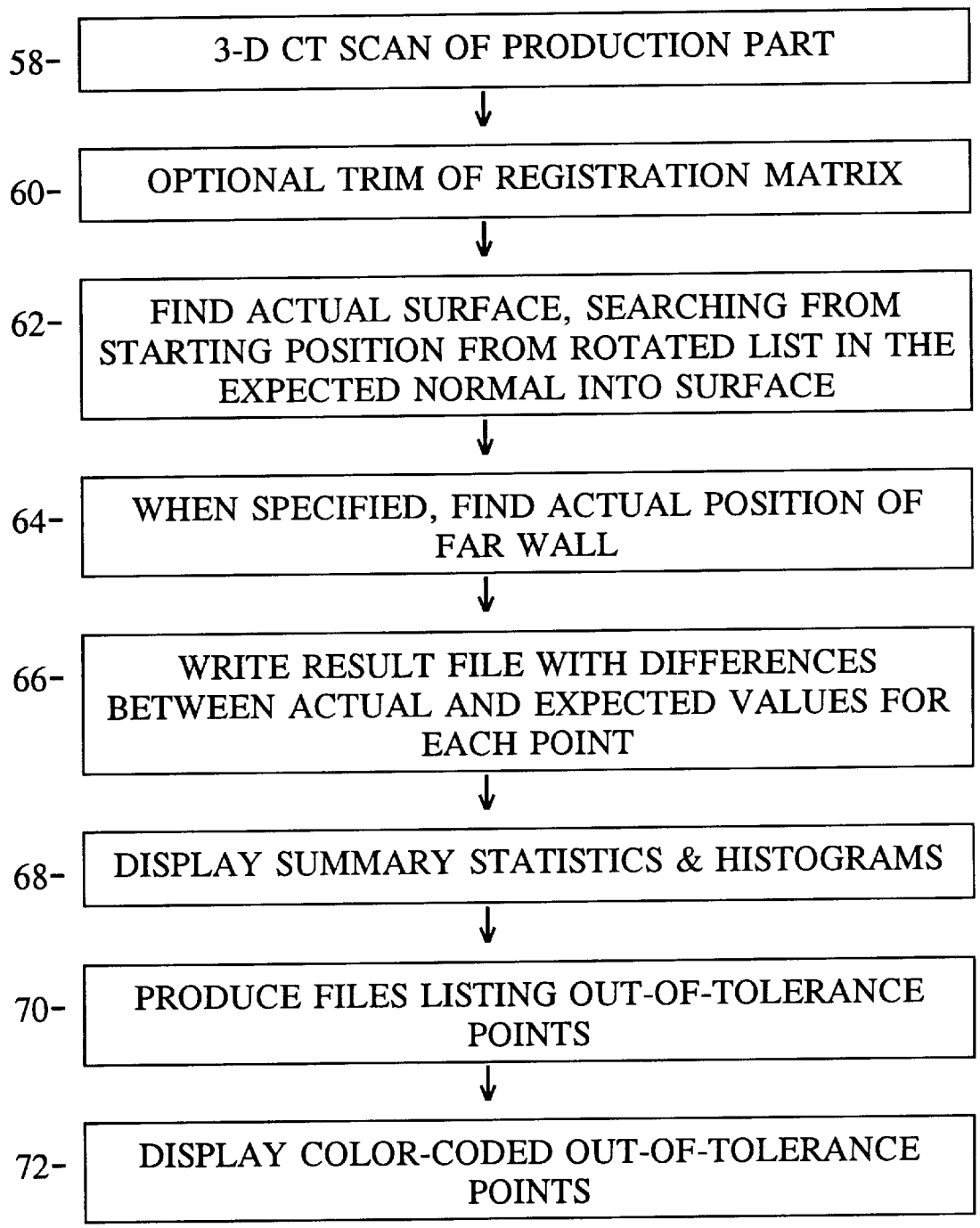

Referring now to FIG. 3, a pre-scanning initializing procedure includes the step 26 of scanning a sample acceptable part and step 28 of generating a sample point list from it. Thereafter, in step 30, the sample point list is transformed into sample scan coordinates for use in comparison with the image of the object to be compared. A preferred alternative embodiment of this step includes the step 26' of utilizing a design of an acceptable object to generate in step 28' a sample point list and transforming that sample point list of the design of an acceptable part into sample scan coordinates for use in comparison with the image of the object to be compared, step 30. While any known design process may be utilized, a preferred embodiment utilizes a CAD design most advantageously.

In either case, in a preferred embodiment, the step of generating a comparison report further comprises the step 32 of using comparison data to allow for minor variations in object placement, creating a report of out-of-tolerance sample points, and creating a color-coded visual display of the out-of-tolerance sample points. These initializing steps calibrate the measurement process to correct not only for CT artifacts, but also for any legitimate deviations in the part-as-manufactured from the nominal design. Such deviations include, but are not limited to, casting flash, normal shrinkage (when not included in the design), production floor tool adjustments, and non-critical areas where dimensional consistency has been deliberately subordinated to other process considerations. The standard which is originally derived from the initializing set can be updated to include results from additional scans as such results accumulate.

Step 34 excludes unsuitable points from the sample list. Step 36 is to scan a production part. Step 38 is to use scan data to trim the registration matrix and step 40 is to measure the surface offset and wall thickness at each point where specified in the sample list.

Additional initializing steps include step 42 the secondary exclusion of surface-offset or thickness measurement at some sample points based on the examination of the example scan of a production part. This allows/provides for the mounting hardware and for any deliberate restrictions of the scanned volume. Optionally, determination (and correction) of the expected measurement bias for each sample point is accomplished for each entry and exit point, computed from the example scan. Or, the typical value seen in a training set of generally-acceptable production parts (which can later be updated to reflect cumulative production results) can be utilized to determine the expected measurement bias for each sample point. Further, the specification of appropriate tolerance ranges may be based on one or more of the part component or region, the expected thickness, and the bias and variations seen in a training set of generally acceptable production parts. This, in the preferred embodiment, would equal four times the inter-quartile distance above and below the mode. Further, in a preferred embodiment, descriptive labels are provided for different sections of the part to be compared and seen in the example scan. These are used in exception reports for production scans.

For each production part or actual part scanned, a total typical time per part for comparison is 5 to 20 minutes. As each actual part is scanned, it is preferred to use the data to trim the registration matrix, step 38, to allow for minor variations in part placement. Further, each actual part scanned is utilized to measure surface offset and wall thickness as specified by the sample-point set, step 40. Additionally, each scan is utilized to tabulate, report, and archive out-of-tolerance points for each parameter by group, with coordinates (and region description) if supplied, step 42. Also, preferably, in step 42 each production part scanned produces out-of-tolerance point sets for color-coded visual display.

Referring now to FIG. 4A, a flow chart illustrating the method of the present invention when a CAD model is available is illustrated. It should be understood that if a CAD design is not available, the example scan, or better, an average from a set of scans which is also used as the initial training set, is used to generate the sample-point list and surface normals. It should be understood that the preparation steps, as set forth in FIGS. 2 and 3 and discussed above, need not be repeated for multiple scans of the same type of part. Again, when a CAD model is available, in a CAD package as is known, the operator would use the stereolithography ("STL") option to produce a surface description of tessellated triangles as an STL file, step 44. In a preferred embodiment, separate files are produced for each portion of the design that may be useful in order to distinguish in specifying examination parameters or in reporting. Next, after reading all of the triangle descriptions into an array, and optionally recursively subdividing any which are inconveniently large, step 46, a set of sample point ("SMP") files are created, step 48, each of which contains, for each triangle in the corresponding input file the following: (1) information about the neighboring triangles in the model, if any, including the surface normals and thus, the implied local curvature in that direction, and (2) a list of coordinates of "sample" points on the triangle, spaced at least as closely as specified, typically about 1 mm. For each sample point, the distance through the model to the first exit surface in the direction opposite the triangle surface normal is computed, step 50, by examination of the triangle list. This distance and the angle between the probe and the exit surface normal are reported with the point. A zero distance is reported if no exit surface is found within the search constraints.

It should be understood that an SMP file can be computationally demanding for large parts, taking several days, even when significant constraints are placed on the exit-search process. For this reason, it has been determined that each SMP record is written with as much information as is available. A subject of that information, and often a subset of the points themselves, is extracted, step 52, by a secondary program to produce one or more comparison point ("CMP") files reflecting various criteria for local curvature, part region, wall flatness, and expected thickness.

Once the relationship between the design coordinates and the scan coordinates has been established, a rotated ("RMP") file is written, step 54, containing the scan coordinates of the comparison points. Optionally, this file is then sorted, step 56, into approximate scan-z order of scan access, which minimizes page faults during the comparison process.

As next indicated in FIG. 4B, production steps are as follows and are repeated after each scan. After the three-dimensional tomographic image has been reconstructed, step 58, and suitable edge threshold established, step 60, the RMP file is read, the "true", i.e., tomographic surface is found, step 62, starting from each comparison point and searching in the direction determined by its surface normal. When specified, step 64, includes finding the actual position of the far wall. A "result" file is written, step 66, with the differences between expected and actual surface location, and also wall thickness, when specified, is determined. Thereafter, the following files are produced, step 68, from the results filed: (1) a set of summary statistics for each tolerance range, (2) histograms of the differences of measurement from design, and (3) point lists in each tolerance and out-of-tolerance range, step 70, in a format suitable for display in the surface program. As is known with CAD design, the surface program is used to display color-coded, out-of-tolerance points, step 72.

Figure 5:
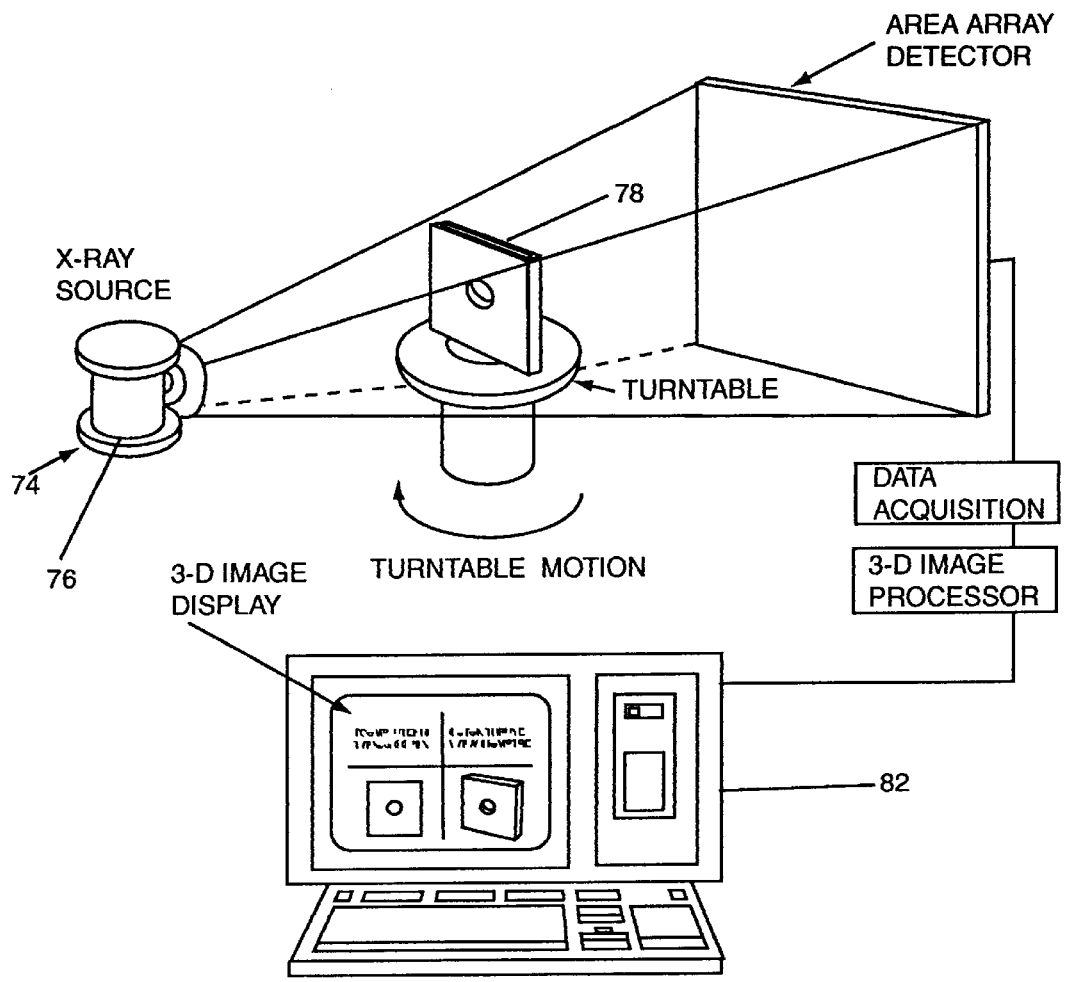
FIG. 5 is an illustration of the apparatus for comparison of the present invention including an x-ray CT scanner and a computer processor.

Referring now to FIG. 5, an illustration of the apparatus for comparison 74 is shown wherein an x-ray CT scanner 76 is utilized for forming a 3-D image of all of the surfaces, exterior and interior of a part 78 to be measured. The x-ray CT scanner 76 is any known device, but preferably the Scientific Measurement Systems, Inc.'s SMARTSCAN brand scanner. The scanning process results in information being received by an area array detector 80 which is then fed into a computer processor 82 for transformation as discussed above. The preferred computer processor 82 is a SUN MICROSYSTEM brand workstation. Any computer processor having the same general characteristics is suitable, however. The computer processor 82 may be used to display the comparisons in 3D, and a hard copy of comparisons may be obtained through utilization of a printer of any known and desired quality, preferably color.

While the apparatus and method for comparison of the present invention has been disclosed in connection with the comparison of parts in particular, it should be appreciated that the comparison system can be used in any other suitable environment. That is, the present invention provides an improved comparison apparatus and method which can be easily manipulated in order, for example, to provide comparisons of any parts or pieces with any desired configuration so as to provide comparative data as to the similarities and differences.

While the present invention has been disclosed in connection with the preferred embodiments thereof, it should be understood that there may be other embodiments which fall within the spirit and scope of the invention as defined by the following claims.

I claim:

1. A method for comparison comprising the steps of:
    (a) obtaining an interior and exterior image of an entire object to be compared by conducting an x-ray CT scan of the entire object;
    (b) creating a standard of measurements for an acceptable object by creating a list of sample points at a specified maximum spacing for all surfaces of an acceptable object and creating a list of wall thickness at each sample point for an acceptable object;
    (c) automatically comparing the image of the object with the standard; and
    (d) generating a comparison report listing deviations of the image of the entire object from the standard for an acceptable object.

2. The method of claim 1 further comprising the steps of determining sample points which are not suitable for measurement of wall thickness and automatically excluding those points from comparison.

3. The method of claim 2 wherein not suitable sample points are selected from a group including:

(a) points in regions of rapid curvature;
    (b) thickness for points where entry and exit normals differ significantly;
    (c) points where thickness is too large to be relevant as a wall measurement; and
    (d) points near free edges.

4. A method for comparing an actual part with a previously created acceptable part comprising the steps of:
    (a) obtaining a 3-D interior and exterior image of the actual part;
    (b) creating a standard of measurements for the acceptable part including creating a list of sample points at a specified maximum spacing for all surfaces for all surfaces and a list of wall thicknesses at each sample point;
    (c) automatically comparing the image of the actual part with the standard; and
    (d) generating a comparison report listing deviations of the image of the actual part from the standard for the acceptable part.

5. The method of claim 4 wherein the step of obtaining a 3-image comprises the step of conducting an x-ray CT scan of the actual part.

6. The method of claim 4 further comprising the steps of determining sample points which are not suitable for measurement of wall thicknesses and automatically excluding those points from comparison.

7. The method of claim 6 wherein not suitable sample points are selected from a group including:
    (a) points in regions of rapid curvature;
    (b) thickness for points where entry and exit normals differ significantly;
    (c) points where thickness is too large to be relevant as a wall measurement; and
    (d) points near free edges.

8. The method of claim 4 wherein the step of creating a standard further comprises the steps of:
    (a) scanning a sample acceptable part and generating a sample point list; and
    (b) transforming the sample point list of the sample acceptable part into sample scan coordinates for use in comparison with the 3-D image of the actual part to be compared.

9. The method of claim 4 wherein the step of creating a standard further comprises the steps of:
    (a) utilizing the design of an acceptable part to generate a sample point list; and
    (b) transforming the sample point list of the design of an acceptable part into sample scan coordinates for use in combination with the 3-D image of the actual part to be compared.

10. The method of claim 4 wherein the step of generating a comparison report further comprises the steps of:
    (a) using comparison data to allow for minor variations in part placement;
    (b) creating a report of out-of-tolerance sample points; and
    (c) creating a color-coded visual display of said out-of-tolerance sample points.

* * * * *